United States Patent [19]
Kutner et al.

[11] Patent Number: 5,817,648
[45] Date of Patent: Oct. 6, 1998

[54] VITAMIN $D_3$ ANALOGUES HAVING AN UNSATURATED SIDE CHAIN

[75] Inventors: Andrzej Kutner; Wanda Wojciechowska, both of Warsaw, Poland; Sebastianus Halkes; Jan-Paul van de Velde, both of Weesp, Netherlands

[73] Assignee: Duphar International Research B.V., Weesp, Netherlands

[21] Appl. No.: 646,640

[22] Filed: May 8, 1996

[30] Foreign Application Priority Data

May 9, 1995 [EP] European Pat. Off. ............. 95201184

[51] Int. Cl.⁶ .......................... A01N 45/02; C07C 401/00
[52] U.S. Cl. ............................................. 514/167; 552/653
[58] Field of Search ................ 514/167; 552/653

[56] References Cited

U.S. PATENT DOCUMENTS

| | | | |
|---|---|---|---|
| 4,237,125 | 12/1980 | Bannai et al. | 424/236 |
| 4,360,471 | 11/1982 | DeLuca et al. | 260/397.2 |
| 4,505,906 | 3/1985 | DeLuca et al. | 514/167 |
| 4,619,920 | 10/1986 | De Luca et al. | 514/167 |
| 5,206,230 | 4/1993 | Ikekawa . | |
| 5,278,155 | 1/1994 | Ikekawa . | |
| 5,403,940 | 4/1995 | Vallés et al. | 549/300 |
| 5,428,029 | 6/1995 | Doran et al. | 514/167 |
| 5,449,668 | 9/1995 | Sestele et al. | 514/167 |

FOREIGN PATENT DOCUMENTS

| | | | |
|---|---|---|---|
| A0633245 | 1/1995 | European Pat. Off. . | |
| 4220757 | 1/1994 | Germany | C07C 401/00 |
| A8910353 | 11/1989 | WIPO . | |
| A9115475 | 10/1991 | WIPO . | |
| 9407851 | 4/1994 | WIPO | C07C 401/00 |

*Primary Examiner*—José G. Dees
*Assistant Examiner*—Alton Pryor
*Attorney, Agent, or Firm*—Watson Cole Stevens Davis, P.L.L.C.

[57] ABSTRACT

Vitamin $D_3$ analogues of the formula (I):

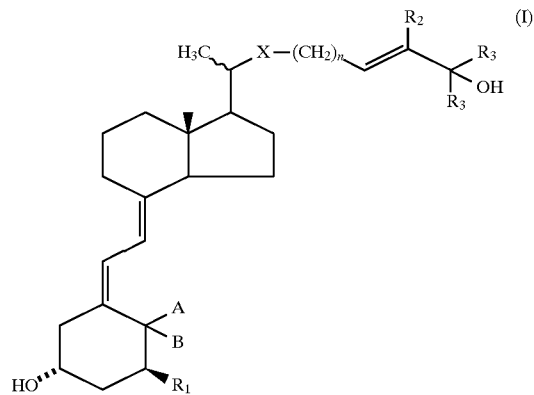

wherein $R_1$ is hydrogen or hydroxy, $R_2$ is hydrogen, $(C_1-C_3)$ alkyl, phenyl, or trifluoromethyl, $R_3$ is branched or unbranched $(C_1-C_4)$ alkyl, cyclopropyl or $CF_3$, A and B are individually hydrogen or methyl, or A and B together form methylene, X is $CH_2$ or O, and n is 2 or 3. These compounds are useful for treating various skin and bone disorders and cancers. These compounds are also useful in cosmetic applications and for diagnostic purposes. Compounds of formula (I) are prepared by reacting a C—25 ester compound with an organometallic compound or by coupling a CD ring ester moiety with a Wittig reagent or an enyne compound to form the desired diene or triene system.

15 Claims, 1 Drawing Sheet

Reaction Scheme A.
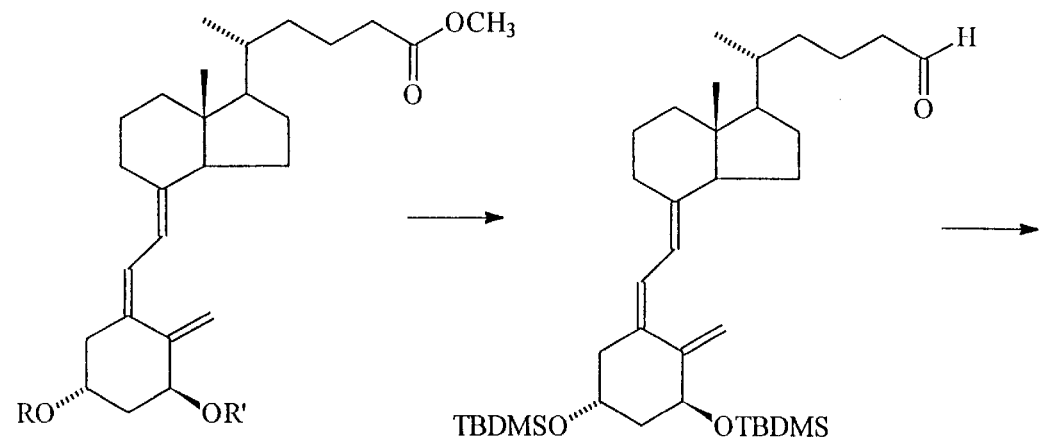
10. R = Ac; R' = H
11. R = R' = H
12. R = R' = TBDMS
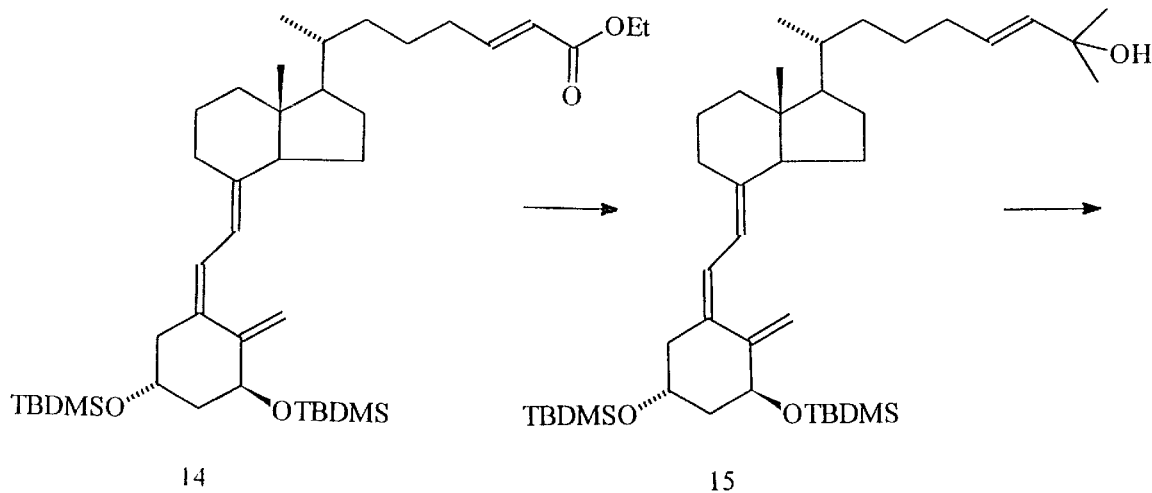
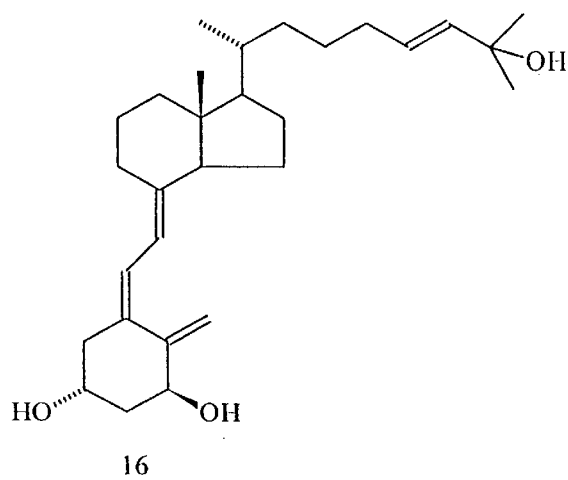

VITAMIN D₃ ANALOGUES HAVING AN UNSATURATED SIDE CHAIN

The invention relates to new vitamin D compounds, to methods of preparing these compounds and to their use in pharmacotherapy and cosmetics. The invention further relates to a valuable new intermediate.

It is generally known, that vitamin-D compounds or vitamin-D related compounds ("vitamin-D compounds") have a strong biological activity and may be used in all those cases in which problems with the calcium metabolism play a part. A few years ago it was found that various active vitamin-D compounds also have other pharmacotherapeutic activities and may be used successfully, for example, for the treatment of certain skin and bone diseases, for cosmetic applications and for treating diseases which are related to cell differentiation, cell proliferation or imbalance in the immune system, including diabetes mellitus, hypertension and inflammatory diseases such as rheumatoid arthritis and asthma. In addition, these compounds may be used in various veterinary applications, and for diagnostic purposes.

Vitamin D compounds which are of interest for the above applications are hydroxylated vitamin D compounds, in particular vitamin D compounds hydroxylated in the 1α-, 24- and/or 25-positions. Recent developments in the field of active vitamin D compounds are 19-nor-vitamin D compounds (EP-A-0387077) and $C_{18}$-modified vitamin D compounds (EP-A-0521550), preferably also hydroxylated in the 1α-position and optionally in the $C_{17}$-side chain. Other modifications of the $C_{17}$-side chain have been proposed, likewise to improve the intended activity and to suppress detrimental side-effects. Examples of modifications of the $C_{17}$-side chain are 22-oxa modifications (e.g. WO 90/09991), fluor substitutions, epoxy groups (e.g. WO 92/21695), etc. In addition certain compounds with elongated side chains (homo compounds) are disclosed in literature, e.g. in the U.S. Pat. Nos. 5,030,772, 5,206,229 and 5,250,523 and in articles by Perlman et al. (*Biochemistry* 1990, 29, 190–6) and by Chodynski and Kutner (*Steroids* 1991, 56, 311–5). Perlman et al. describe the insertion of a trans double bond at C-22 of 24-homologated analogs. This double bond insertion, however, does not significantly affect the activities compared with the respective analogs with saturated side chain. It has appeared, however, that trans-position of the double bond in the natural C-22 position to the C-24 position, as described by Chodynski and Kutner, does not result in the intended improvement in selectivity. Generally spoken, the above $C_{17}$-side chain modified vitamin D compounds are still not completely satisfactory as regards their selective activity, i.e. the intended activity without detrimental side-effects.

Further, the accessibility of the $C_{17}$-side chain modified compounds is often insufficient or unattractive. In the synthesis of said $C_{17}$-side chain modified vitamin D compounds often a large number of laborious synthetic steps are involved and starting materials are often not readily available.

As a matter of fact, both the starting compounds for the preparation of such vitamin-D compounds must be easily available or accessible, and the multistep preparation process must lead to the intended purpose with sufficient selectivity and efficiency.

It is therefore the objective of the present invention to provide a new class of vitamin D compounds, having selective biological properties, and which is well accessible from readily available or accessible starting materials.

According to the present invention this objective can be achieved with a new vitamin D compound of the general formula

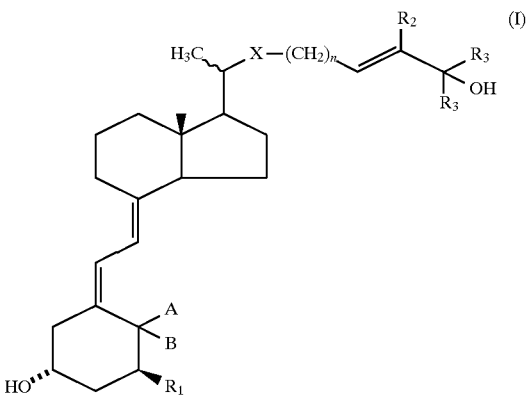

wherein:
$R_1$ is a hydrogen atom or a hydroxy group,
$R_2$ is a hydrogen atom or a substituent selected from the group consisting of $(C_1-C_3)$alkyl, phenyl and trifluoromethyl,
$R_3$ is a branched or unbranched $(C_1-C_4)$alkyl group, a cyclopropyl group or a $CF_3$ group,
A and B are each individually hydrogen atoms or methyl groups, or
A and B form together a methylene group,
X is $CH_2$ or O
n is 2 or 3.

The above new vitamin D compounds of the invention, presented by the general formula I, are valuable substances. The biological results, as illustrated in the Examples, indicate that these compounds are promising as biologically active substances and may be used in all above-mentioned pharmacotherapeutic indications, more in particular for the treatment of osteoporosis, renal osteodystrophy, osteomalacia, skin disorders such as psoriasis (and other hyperproliferative skin diseases), eczema and dermatitis, myopathy, leukaemia, breast and colon cancer, osteosarcomas, squamous cell carcinomas, melanoma, certain immunological disorders, and transplant rejections. In comparison with a chemically related (24E)-24,24a-dehydro-24,24-dihomo compound, as described by Chodynski and Kutner (*Steroids* 1991, 56, 311–5), the compounds of the invention have superior biological activity, in particular for the above-defined indications.

Furthermore, the new vitamin D compounds of the invention may be used for wound healing and may be incorporated in cosmetic compositions, such as creams, lotions, ointments and the like, in order to preserve, condition and/or protect the skin and to improve various skin conditions, such as wrinkles, dry skin, skin slackness and insufficient sebum secretion. The new vitamin D compounds may also be used for diagnostic purposes.

Suitable examples of the above substituent $R_3$ are methyl, trifluoromethyl, ethyl, isopropyl and cyclopropyl.

A vitamin D compound is preferred, having the general formula I, wherein:
$R_1$ is a hydroxy group,
$R_2$ is hydrogen or methyl,
$R_3$ is methyl, ethyl, isopropyl or cyclopropyl,
X is $CH_2$,
A and B are each individually hydrogen atoms or form together a methylene group,
n is 2.

It is a special merit of the present invention that the above new vitamin D compounds of the invention can easily be prepared from readily available starting materials. In particular, it has been found, that the desired attachment of the appropriate substituents to $C_{25}$, can easily be achieved by starting from a readily accessible ester compound.

Consequently, the invention also relates to a method of preparing a vitamin D compound of the general formula I, as defined above, which method is characterized according to the present invention, in that an ester compound of the general formula

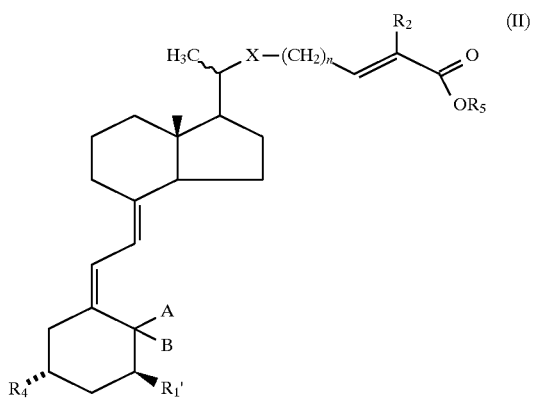

wherein:

$R_1'$ is a hydrogen atom or a protected hydroxy group, $R_2$, A, B, X and n have the above defined meanings, $R_4$ is a protected hydroxy group, and $R_5$ is a $(C_1–C_6)$alkyl group;

is reacted with an organometallic compound of the general formula $$R_3M(X)_p \qquad (III)$$

wherein:

$R_3$ has the above defined meaning,

X is Cl, Br or I,

M is a metal selected from Li and Mg, and p is, dependent on the valence of M, 0 or 1;

followed by deprotection.

Suitable examples of organometallic compounds of the above general formula III are lithium compounds, such as isopropyllithium, cyclopropyllithium and ethyllithium, and Grignard reagents, such as isopropylmagnesium chloride, cyclopropylmagnesium chloride and methylmagnesium chloride, as well as the corresponding bromides and iodides.

In an equally attractive manner, compounds of formula I can be build-up from a CD ring moiety with a finalized $C_{17}$-side chain, followed by coupling with an A ring moiety in such a way that the desired diene or triene system is formed. Therefore the invention also relates to a method of preparing a vitamin D compound as defined above, which method is characterized according to the present invention, in that an ester compound of the general formula

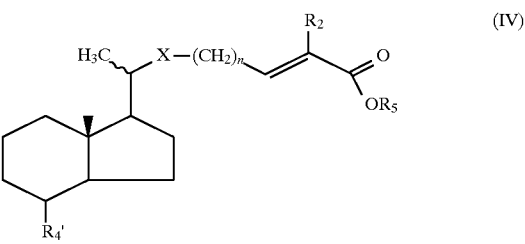

wherein:

$R_2$, $R_5$, X and n have the above defined meanings, $R_4'$ is an optionally protected hydroxy group;

is reacted with an organometallic compound of the general formula $$R_3M(X)_p \qquad (III)$$

wherein the symbols have the above defined meanings; after which the hydrindane compound obtained, having the general formula

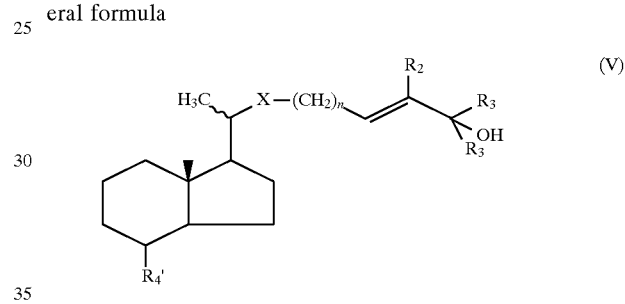

is deprotected, if $R_4'$ is a protected hydroxy group, and then oxidized to the corresponding hydrindane-4-one compound of the general formula

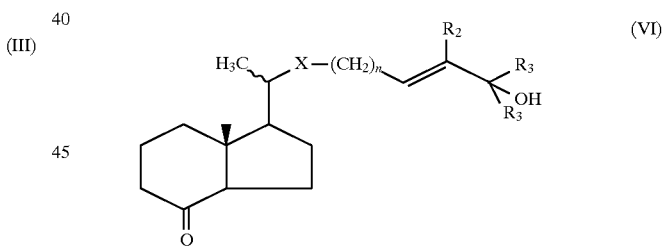

which compound of formula VI, if desired after protection of the hydroxy group, is then converted either (a) with a Wittig reagent of the general formula

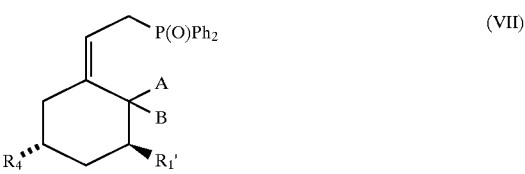

wherein:

$R_1'$, $R_4$, A and B have the above defined meanings; and or (b), after enolization and derivatization of the enolic hydroxy group, with an enyne compound of the general formula

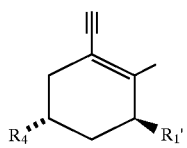

(VIII)

wherein $R_1'$ and $R_4$ have the above meanings, followed by hydrogenation and isomerization, to produce a compound of the general formula I, wherein A and B form together a methylene group; followed by deprotection.

Hydroxy groups in the starting compounds or reactants may be protected by a reaction with a suitable esterification or etherification agent. A suitable esterification agent is an alkylchlorocarbonate having 2 to 5 carbon atoms, or an aromatic carboxylic acid or saturated aliphatic carboxylic acid having 1 to 4 carbon atoms such as benzoic acid, or a derivative of such acids suitable for the esterification reaction. In order to protect hydroxy groups in the form of an ether, in principle any etherification agent known for this purpose is suitable: for example, a trialkylsilylimidazole, a trialkylsilylhalide, a trialkylsilyltriflate (-trifluoromethanesulfonate), a diphenylalkylsilylhalide, methoxymethylchloride or a diphenylalkylsilyltriflate, or a derivative thereof, the alkyl groups of which have 1 to 6 carbon atoms.

Particularly suitable for this purpose are trimethylsilylchloride, tert.-butyldimethylsilylchloride, dimethyl-(1,1,2-trimethylpropyl)-silylchloride, tert.-butyldimethylsilyl triflate, or trimethylsilylimidazole, because these etherification agents readily react with the hydroxy group to be protected to form an ether function, which on the one hand is sufficiently stable under the conditions of the reaction or reactions in view, but on the other hand can easily be removed [deprotection] to recover the original hydroxy group; tert.-butyldimethylsilylchloride or triflate is to be preferred, because these groups have been found to be excellently suitable as a protective group.

The enolic hydroxy group of enolized compound VI is preferably derivatized by a reaction with N-aryltriflimide to produce a triflate. Suitable examples of aryl groups are phenyl and chloropyridyl.

The hydrindane-4-one compound VI is prepared by oxidizing a hydrindane compound V, with an oxidizing agent, preferably selected from a chromium-containing oxidant such as pyridinium chlorochromate or pyridinium dichromate, and ruthenium tetroxide.

The intermediate ester compound of the general formula II, presented above, is new. Therefore the present invention also relates to this intermediate, as well as to methods of preparing this compound.

The ester compound of the general formula II, wherein A and B together form a methylene group, can conveniently be prepared by reacting an ester of the general formula

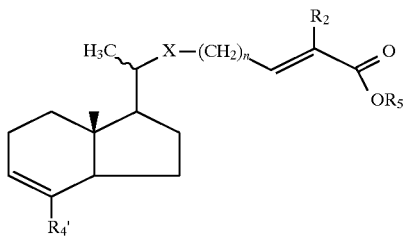

(IX)

wherein:
$R_2$, $R_5$, X and n have the above defined meanings, and $R_6$ is a derivatized hydroxy group;

is reacted with an enyne compound of the general formula

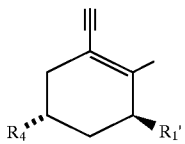

(VIII)

wherein $R_1'$ and $R_4$ have the above defined meanings; followed by hydrogenation and isomerization.

This reaction is preferably carried out in two reaction steps, viz. by first reacting the ingredients under the influence of an organic base such as triethylamine, and in the presence of a palladium catalyst such as $(PPh_3)_2PdCl_2$, and by then subjecting the product obtained to a hydrogenation with hydrogen under the influence of a suitable catalyst such as Lindlar catalyst (Pd on $CaCO_3$, poisoned with lead), followed by an isomerization of the previtamin configuration obtained to the vitamin structure of the general formula II.

Alternatively, said ester compound of the general formula IX can easily be synthesized by reacting a modified Windaus Grundmann ketone of the general formula

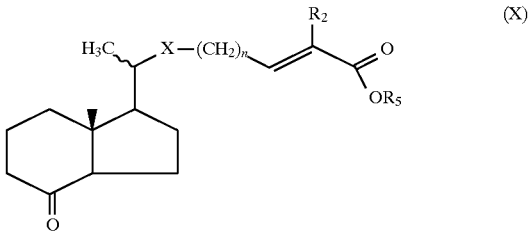

(X)

wherein:
$R_2$, $R_5$, X and n have the above defined meanings; with a Wittig reagent of the general formula

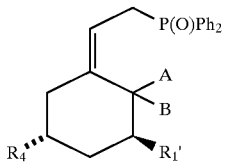

(VII)

wherein:
$R_1'$, $R_4$, A and B have the above defined meanings.

In a further alternative for the preparation of the intermediate ester compound of the general formula II, a compound of the general formula

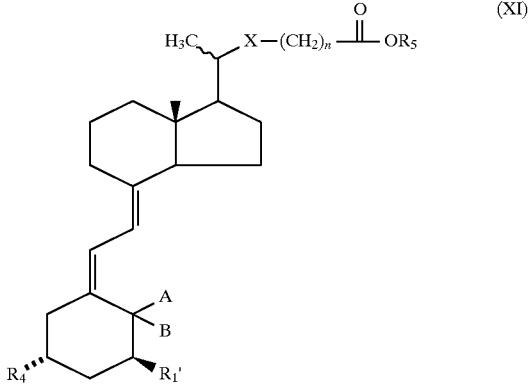

(XI)

is reacted with a reducing agent, after which the compound obtained, having the general formula

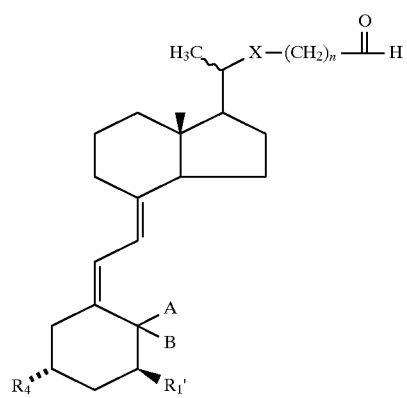

is converted with a compound of the general formula

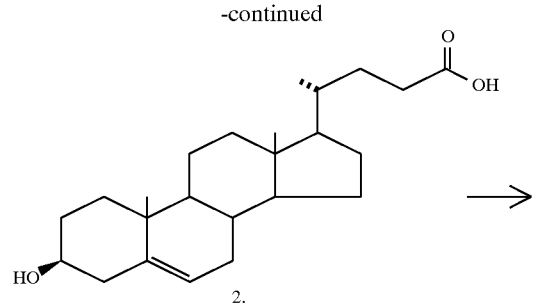

wherein:

$R_2$ and $R_5$ have the above defined meanings, $R_7$ is a substituent selected from the group consisting of branched or unbranched ($C_1$–$C_4$)alkoxy, phenoxy, phenyl or di($C_1$–$C_4$)alkylamino, and q is 0 or 1 if n is 1 and q is 0 if n is 2.

The reduction of compounds XI can be performed with different reducing agents, such as metal alkyl hydrides. The preferred reducing agent is diisobutylaluminium hydride.

The starting compounds of formula XI can be conveniently prepared from readily available substances, e.g. for the synthesis of the vitamin D compound wherein X=$CH_2$, n=2 and A and B form together a methylene group, as depicted in FIG. 1 from the readily available hyodeoxycholic acid 1 by methods well-known in the art, starting with introduction of the $\Delta_5$ bond by dehydratation followed by one-carbon homologation of the side chain (e.g. by Arndt-Eistert diazo-ketone synthesis), esterification, introduction of the $\Delta_{5,7}$ system by bromination/dehydrobromination and secosteroid formation by UV irradiation to yield compound 6. Compound 6 can be converted into compound 10 according to the method described by Ryznar (*Acta Pol. Pharm.* 1988, 45, 214–8).

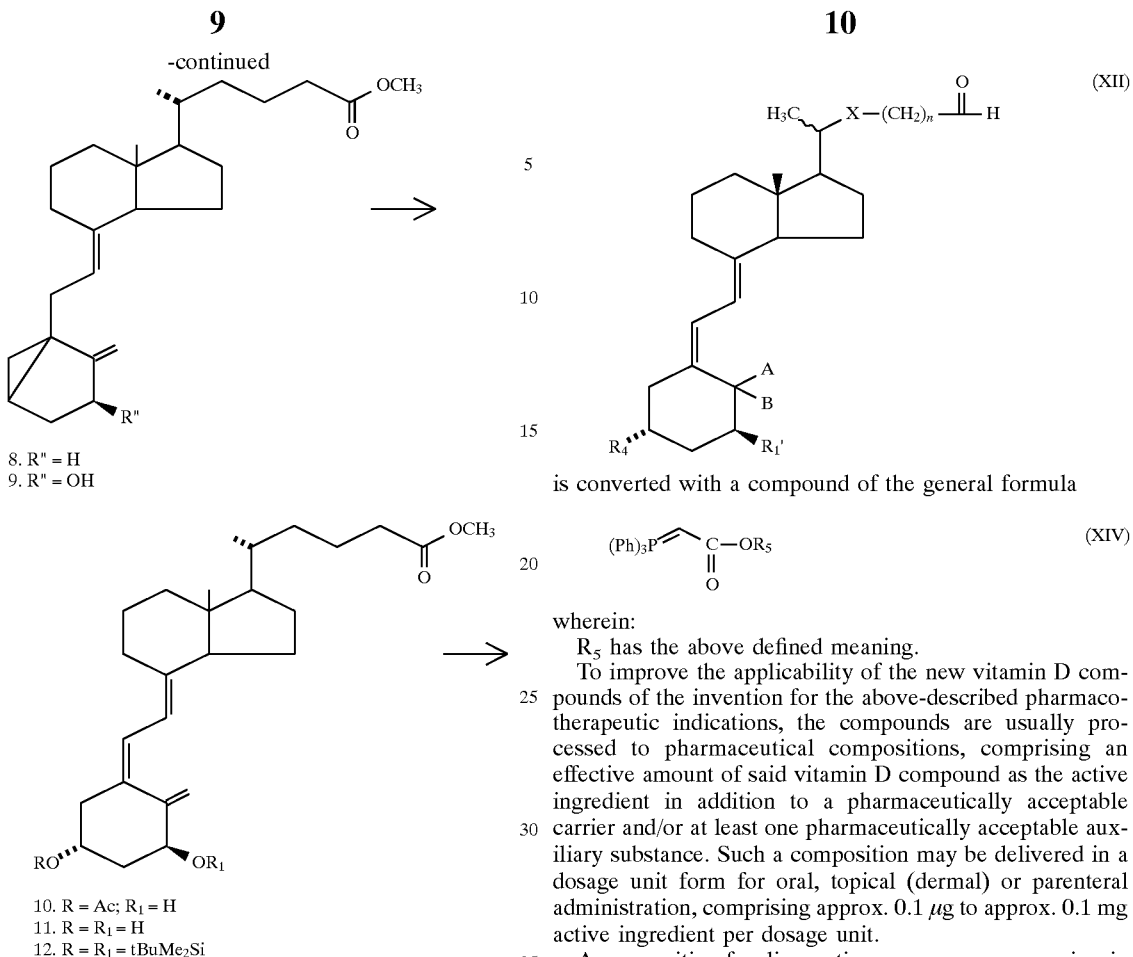

8. R" = H
9. R" = OH

10. R = Ac; R₁ = H
11. R = R₁ = H
12. R = R₁ = tBuMe₂Si

FIG. 1.

The Wittig reagents of formula XIII can be prepared according to methods known in the art. Preferred substituent $R_7$ is the ethoxy group.

In a further alternative for the preparation of the intermediate ester compound of the general formula II, a compound of the general formula

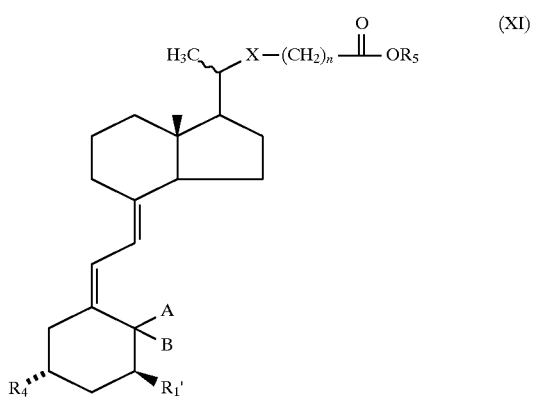

is reacted with a reducing agent, after which the compound obtained, having the general formula $$H_3C\underset{}{\overset{}{\diagdown}}X-(CH_2)_n-\underset{O}{\overset{\|}{C}}-H \qquad (XII)$$

is converted with a compound of the general formula $$(Ph)_3P\diagup\overset{}{C}-OR_5 \qquad (XIV)$$
$$\underset{O}{\overset{\|}{}}$$

wherein:
$R_5$ has the above defined meaning.

To improve the applicability of the new vitamin D compounds of the invention for the above-described pharmacotherapeutic indications, the compounds are usually processed to pharmaceutical compositions, comprising an effective amount of said vitamin D compound as the active ingredient in addition to a pharmaceutically acceptable carrier and/or at least one pharmaceutically acceptable auxiliary substance. Such a composition may be delivered in a dosage unit form for oral, topical (dermal) or parenteral administration, comprising approx. 0.1 µg to approx. 0.1 mg active ingredient per dosage unit.

A composition for diagnostic purposes may comprise, in addition to the vitamin D compound of the present invention, a compatible, non-toxic carrier and/or at least one auxiliary substance.

A cosmetical composition may comprise, in addition to an effective amount (in the range of approx. 0.1 µg to approx. 0.1 mg per dosage unit in a dosage unit form) of the vitamin D compound of the present invention, a cosmetically acceptable, non-toxic carrier and/or at least one auxiliary substance.

Finally the invention relates to a method for the treatment and prophylaxis of a number of disease states including autoiummune diseases (including diabetes mellitus), acne, alopecia, skin aging (including photo-aging), imbalance in the immune system, inflammatory diseases such as rheumatoid arthritis and asthma, as well as diseases related to abnormal cell differentiation and/or proliferation, in a warm-blooded living being, comprising administering to said being or treating said being with a pharmaceutical composition as defined above in a quantity effective for the intended purpose. Examples of such diseases are psoriasis and other hyperproliferative skin diseases.

The present invention also relates to the use of the above pharmaceutical compositions for the treatment of solid, skin and blood cancers, in particular of blood cancers such as leukaemia, of breast cancer, and of skin cancers such as melanoma and squamous cell carcinoma.

The above-defined cosmetical compositions, in particular selected from the group consisting of creams, lotions, ointments, liposomes and gels, can be used for the treatment and prevention of a number of skin disorders, such as inadequate skin firmness or texture, insufficient skin hydration, wrinkles and insufficient sebum secretion.

The invention will now be described in greater detail with reference to the following specific Examples.

The following abbreviations are used in the examples:
THF=tetrahydrofuran
TBDMS=tert.-butyl dimethyl silyl
DMF=N,N-dimethylformamide
Ac=acetyl

EXAMPLES

Example I

Preparation of (5Z,7E)-(1S,3R)-9,10-Seco-24a,24b-dihomo-(24aE)-5,7,10(19),24a-cholestatetraen-1,3, 25-triol 16.

The reaction equation is presented in the Reaction Scheme A appended.

(a) Preparation of Compound 11

To the solution of 1.8 g (3.9 mmol) of ester 10 in 108 ml THF, 108 ml of a 0.1N methanolic solution of KOH is added. The mixture is stirred at room temperature until no substrate is observed on TLC (about 3 hours). The mixture is neutralized with 10 ml of 1N HCl. Removal of solvents and extraction with ethyl acetates gives 1.57 g (96% yield) of dihydroxyester 11 in the form of a colourless oil. The product 11 is identified by IR and $^1$H-NMR.

IR (CHCl$_3$): 3450, 2950, 2890, 1705 cm$^{-1}$.

$^1$H-NMR (CDCl$_3$, δ): 0.54 (3H, s, 18-CH3), 3.66 (3H, s, COOCH$_3$), 4.17 (1H, m, 3-H), 4.40 (1H, m, 1-H), 4.99 (1H, s, 19Z-H), 5.32 (1H, s, 19E-H), 6.04 (br d, J=11 Hz, 7-H), 6.35 (br d, J=11 Hz, 6-H) ppm.

(b). Preparation of Compound 12

Imidazole (1.3 g, 22.8 mmol) and 1.3 g (8.7 mmol) of t-butyldimethylsilyl chloride are added to a solution of 1.5 g (3.6 mmol) of dihydroxyester 11 in 10 ml of DMF. The mixture is stirred at room temperature until no substrate is detected by TLC (about 2.5 hours). Extraction with hexane/ethylacetate 4/1 and gel filtration gives 2.15 g (93% yield) of disilylated ester 12 in the form of a coulorless oil. The product 12 is identified by UV, IR and $^1$H-NMR.

UV (hexane): $\lambda_{max}$=264.8 nm.

IR (CHCl$_3$): 2950, 2860, 1705 cm$^{-1}$.

$^1$H-NMR (CDCl$_3$, δ): 0.06 (12H, b s, Si—CH$_3$), 0.53 (3H, s, 18-CH$_3$), 0.87 (18H, b s, C—CH$_3$), 3.66 (3H, s, —COOCH$_3$), 4.17 (1H, m, 3-H), 4.4 (1H, m, 1-H), 4.86 (1H, b s, J$_{gem}$=1.8 Hz, 19Z-H), 5.18 (1H, b s, J$_{gem}$=1.8 Hz, 19E-H), 6.02 (br d, J=11 Hz, 7-H), 6.35 (br d, J=11 Hz, 6-H) ppm.

(c) Preparation of Compound 13

Diisobutylaluminium hydride (1M, 750 μl, 0.75 mmol) is added under argon to a solution of 500 mg (0.77 mmol) of disilylated ester 12 in 2.5 ml of toluene, at −70° C., dropwise, to keep the temperature below −60° C. The mixture is stirred at −65° C. until no substrate is detected by TLC (about 3 hours). Work-up of the reaction mixture, Celite filtration and silica gel chromatography give 330 mg (69% yield) of aldehyde 13 in the form of a colourless oil and 50 mg (11% yield) of C-24a alcohol as a byproduct. The compound 13 is identified by UV, IR, $^1$H-NMR, $^{13}$C-NMR and EIMS.

UV (hexane): $\lambda_{max}$=264.6 nm.

IR (CHCl$_3$): 2930, 1722, 1645 cm$^{-1}$.

$^1$H-NMR (CDCl$_3$, δ): 0.049 (12H, b s, SiCH$_3$), 0.51 (3H, s, 18-CH$_3$), 0.86 (18H, b s, C—CH$_3$), 4.2 (1H, m, 3-H), 4.3 (1H, m, 1-H), 4.84 (1H, b s, J$_{gem}$=2.3 Hz, 19Z-H), 5.15 (1H, b s, J$_{gem}$=2.3 Hz, 19E-H), 6.02 (br d, J=11 Hz, 7-H), 6.35 (br d, J=11 Hz, 6-H), 9.74 (1H, t, J=1.8 Hz, CHO) ppm.

$^{13}$C-NMR (CDCl$_3$, δ): −5.09, −4.80, −4.69, 11.94, 18.15, 18.22, 18.69, 22.11, 23.36, 25.79, 25.84, 27.68, 28.84, 35.39, 35.97, 40.56, 44.32, 44.78, 45.75, 46.01, 56.19, 56.28, 67.49, 72.04, 77.21, 111.22, 117.90, 123.12, 134.99, 140.91, 148.25, 202.97 ppm.

EIMS (m/z): 614 (M$^+$), 482 (100), 248 (95); calc. for C$_{37}$H$_{66}$O$_3$Si$_2$ 614.4546, found 614.4551.

(d). Preparation of Compound 14

A solution of 89 mg (0.145 mmol) of aldehyde 13 in 2 ml THF is added to a solution of 70 mg (0.2 mmol) of ethoxycarbonylmethylenetriphenyl phosphorane in 2 ml THF under argon at room temperature. The mixture is stirred for 16 hours at room temperature. Silicagel chromatography gives 102 mg (91% yield) of ester 14 as a colourless oil. The compound 14 is identified by UV, IR, $^1$H-NMR and $^{13}$C-NMR.

UV (hexane): $\lambda_{max}$=264.6 nm.

IR (CHCl$_3$): 2951, 1708, 1652 cm$^{-1}$.

$^1$H-NMR (CDCl$_3$, δ): 0.049 (12H, b s, Si—CH$_3$), 0.52 (3H, s, 18-CH$_3$), 0.89 (18H, b s, C—CH$_3$), 1.27 (3H, t, J=7.1 Hz, —CH$_2$CH$_3$), 4.2 (1H, m, 3-H), 4.3 (1H, m, 1-H), 4.84 (1H, b s, J$_{gem}$=2.4 Hz, 19Z-H), 5.15 (1H, b s, J$_{gem}$=2.4 Hz, 19E-H), 5.78 (1H, d t, J$_{trans}$=15.7 Hz, J$_{vic}$=1.4 Hz, 24b-H), 6.02 (br d, J=11 Hz, 7-H), 6.35 (br d, J=11 Hz, 6-H), 6.90 (1H, d t, J$_{trans}$=15.8 Hz, J$_{vic}$=7.2 Hz, 24a-H) ppm.

$^3$C-NMR (CDCl$_3$, δ): −5.05, −4.77, −4.66, 11.98, 14.27, 18.13, 18.23, 18.79, 22.17, 23.50, 24.76, 25.84, 27.69, 28.89, 32.64, 35.51, 35.98, 40.67, 44.90, 45.81, 46.10, 56.37, 56.52, 60.06, 67.57, 72.11, 111.15, 117.97, 121.30, 123.17, 135.06, 140.93, 148.44, 149.37 ppm.

(e). Preparation of Compound 15

Ester 14 (60 mg, 0.088 mmol) in 1 ml of THF is added to a solution of methylmagnesium bromide in diethyl ether (0.1 ml, 0.3 mmol) diluted with 0.75 ml of THF, under argon at room temperature. The mixture is stirred for 24 hours at room temperature. Silicagel chromatography gives 31.3 mg (54% yield) of alcohol 15 as a colourless oil.

(f). Preparation of Compound 16

A solution of 31 mg (0.046 mmol) of alcohol 15 in 1 ml of THF is added, under argon, to a solution of 315 mg (1 mmol) tetrabutylammonium fluoride in 1 ml of THF. The mixture is stirred at room temperature until no substrate is detected on TLC (about 16 hours). Extraction with ethyl acetate followed by silicagel chromatography gives 19.3 mg (94% yield) of triol 16 as a colourless oil. The product 16 is identified by UV, $^1$H-NMR and EIMS.

UV (hexane): $\lambda_{max}$=263.8 nm.

$^1$H-NMR (CDCl$_3$, δ): 0.54 (3H, s, 18-CH$_3$), 1.31 (6H, s, 26,27-CH$_3$), 4.2 (1H, m, 3-H), 4.4 (1H, m, 1-H), 5.0 (1H, b s, 19Z-H), 5.3 (1H, t, J$_{gem}$=1.7 Hz, 19E-H), 5.85 (1H, d, J$_{trans}$=16.0 Hz, 24b-H), 6.02 (br d, J=11 Hz, 7-H), 6.35 (br d, J=11 Hz, 6-H), 7.1 (1H, m, J$_{trans}$=16 Hz, 24b-H) ppm.

EIMS (m/z): 442 (M$^+$, 39), 424 (M$^+$−H$_2$O, 95), 406 (M$^+$−2H$_2$O, 93), 388 (M$^+$−3H$_2$O, 100), 285 (100); calc. for C$_{29}$H$_{46}$O$_3$ 442.3447, found 442.3440.

Example II

Affinity to Intracellular Vitamin D Receptor

Vitamin D compounds according to the invention are dissolved in ethanol in concentrations ranging from $10^{-13}$ to $10^{-7}$M. The affinity towards the calf thymus intracellular vitamin D receptor (VDR) is determined in a biological assay. In this assay, $^3$H-1α,25-dihydroxycholecalciferol ($^3$H-1α,25-DHCC), which is specifically bound to the VDR, is replaced by the tested compounds. Whereas the known 24,24-dihomo-Δ(24-24a)calcitriol has a substantially lower affinity ($\leq 1\%$) towards the VDR than calcitriol, 24,24-dihomo-Δ(24a-24b)calcitriol (compound 16 of Example I) has a surprisingly high affinity towards the VDR, viz. 9 times that of calcitriol. A high affinity towards the VDR is indicative for biologically active compounds.

Example III

Affinity to Vitamin D Binding Protein

Vitamin D binding protein (DBP) is the specific carrier for vitamin D and its metabolites in blood. The biological activity of vitamin D compounds depends on their binding to DBP, because strong binding to DBP will reduce the intracellular access to the VDR. Binding to the DBP may also influence the half-life of the vitamin D derivatives in circulation. Weak binders are rapidly metabolized, which is a favourable aspect in topical application.

In the assay, DBP is incubated with $^3$H-1α,25-DHCC and 1α,25-DHCC or with the vitamin D compounds to be investigated. To this purpose, the vitamin compounds are dissolved in ethanol in concentrations ranging from $10^{-11}$ to $2.5 \times 10^6$M. The percentage bound/unbound $^3$H-1α,25-DHCC is then calculated. DBP is purified from total human serum. Both 24,24-dihomo-Δ(24-24a)-calcitriol and 24,24-dihomo-Δ(24a-24b)-calcitriol are much weaker binders to the DBP than calcitriol (2% and 3.5% respectively).

Example IV

Cell Differentiation

The vitamin D compounds to be investigated are dissolved in ethanol in concentrations ranging from $10^{-12}$ to $10^{-6}$M and tested for their capacity to induce cell differentiation in a HL-60 assay. In this assay, biochemical examination of the human leukemic cell line HL-60 is performed, in order to establish whether cell differentiation has taken place.

Differentiation is expressed as the maturation parameter nitroblue tetrazolium (NBT) reduction. After culturing with the known calcitriol or with the vitamin D compounds to be investigated, the percentage of cells containing black formazan deposits is determined. An increase in the percentage of NBT reducing cells indicates an increase in cell differentiation.

Proliferation and vitality of the cell cultures are established by counting the number of cells and by the trypan blue exclusion method. The vitality and proliferation of the cells in the HL-60 cultures were good in all tests. Calcitriol (known), and 24,24-dihomo-Δ(24a-24b)-calcitriol are equally active in inducing differentiation and maturation of the HL-60 cells, whereas the known 24,24-dihomo-Δ(24-24a)-calcitriol is 4 times less active. The optimal effect is found at concentrations between $10^{-7}$ and $10^{-6}$M.

We claim:

1. A vitamin D compound of the general formula

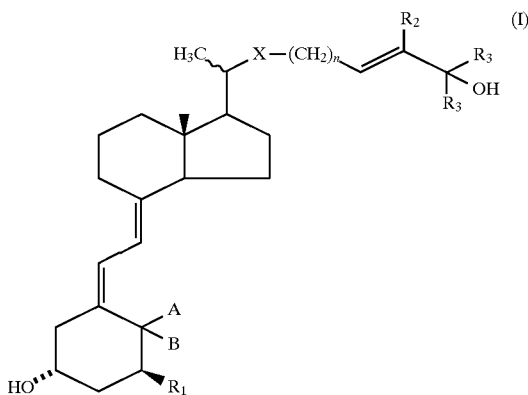

wherein:
- $R^1$ is a hydrogen atom or a hydroxy group,
- $R_2$ is a hydrogen atom or a substituent selected from the group consisting of ($C_1$–$C_3$)alkyl, phenyl and trifluoromethyl,
- $R_3$ is a branched or unbranched ($C_1$–$C_4$)alkyl group, a cyclopropyl group or a $CF_3$ group,
- A and B are each individually hydrogen atoms or methyl groups, or
- A and B form together a methylene group,
- X is $CH_2$ or O,
- n is 2 or 3.

2. A vitamin D compound as claimed in claim 1, having the general formula I as shown in claim 1, wherein:
- $R_1$ is a hydroxy group,
- $R_2$ is hydrogen or methyl,
- $R_3$ is methyl, ethyl, isopropyl or cyclopropyl,
- X is $CH_2$,
- A and B are each individually hydrogen atoms or form together a methylene group,
- n is 2.

3. A method of preparing a vitamin D compound as claimed in claim 1, characterized in that an ester compound of the general formula

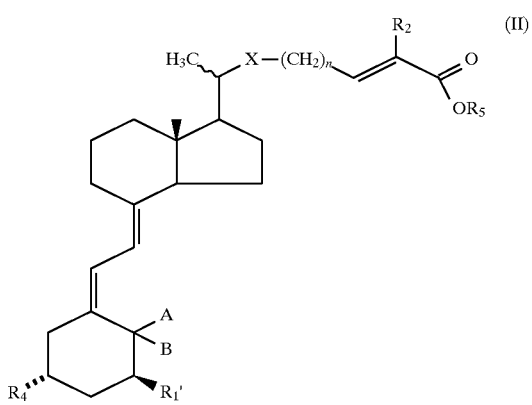

wherein:
- $R_1'$ is a hydrogen atom or a protected hydroxy group,
- $R_2$, A, B, X and n have meanings given in claim 1,
- $R_4$ is a protected hydroxy group, and
- $R_5$ is a ($C_1$–$C_6$)alkyl group;

is reacted with an organometallic compound of the general formula $$R_3M(X)_p \quad (III)$$

wherein:

R$_3$ has the meaning given in claim 1,
X is Cl, Br or I,
M is a metal selected from Li and Mg, and
p is, dependent on the valence of M, 0 or 1;

followed by deprotection.

4. A method of preparing a vitamin D compound as claimed in claim 1, characterized in that an ester compound of the general formula

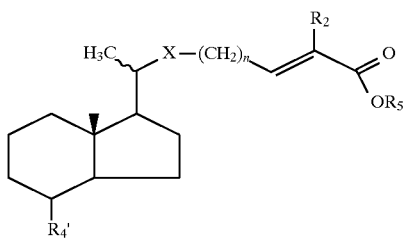
(IV)

wherein:

R$_2$, X and n have the meanings given in claim 1,
R$_4$' is an optionally protected hydroxy group, and
R$_5$ has the meaning given in claim 3;

is reacted with an organometallic compound of the general formula $$R_3M(X)_p \quad (III)$$

wherein the symbols have the meanings given in claim 3; after which the hydrindane compound obtained, having the general formula

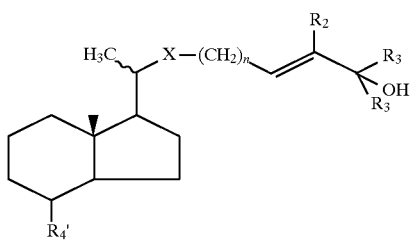
(V)

is deprotected, if R$_4$' is a protected hydroxy group, and then oxidized to the corresponding hydrindane-4-one compound of the general formula

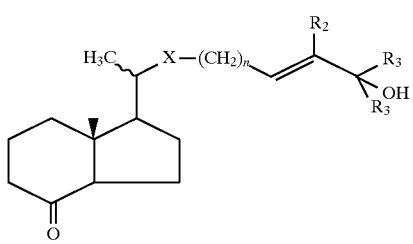
(VI)

which compound of formula VI is then converted either (a) with a Wittig reagent of the general formula

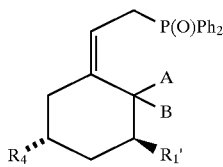
(VII)

wherein:

R$_1$' and R$_4$ have the meanings given in claim 3, and
A and B have the meanings given in claim 1;

or (b), after enolization and derivatization of the enolic hydroxy group, with an enyne compound of the general formula

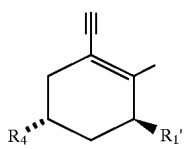
(VIII)

wherein R$_1$' and R$_4$ have the above meanings, followed by hydrogenation and isomerization, to produce a compound of the general formula I, wherein A and B form together a methylene group; followed by deprotection.

5. The method of claim 4, further comprising, before the converting step, protecting the hydroxy group of the compound of formula VI.

6. A vitamin D compound as claimed in claim 2, wherein R$_2$ is hydrogen, R$_3$ is methyl, and A and B form together a methylene group.

7. A pharmaceutical composition comprising, in addition to a pharmaceutically acceptable carrier as the active ingredient at least one compound as defined in claim 1 or 2 in an effective amount.

8. An ester compound of the general formula II:

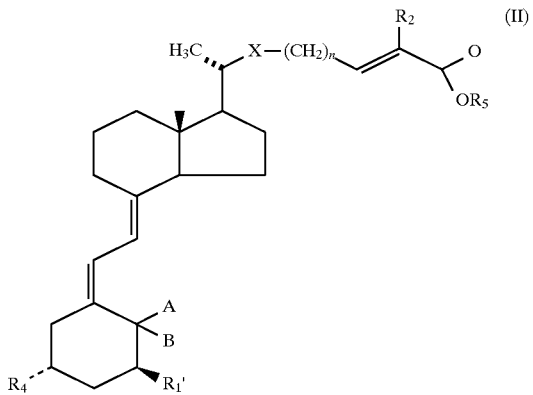
(II)

wherein:

R'$_1$ is a hydrogen atom or a protected hydroxy group,
R$_2$ is a hydrogen atom or a substituent selected from the group consisting of (C$_1$–C$_3$)alkyl, phenyl and trifluoromethyl,
R$_3$ is a branched or unbranched (C$_1$–C$_4$)alkyl group, a cyclopropyl group or CF$_3$ group,
A and B are each individually hydrogen atoms or methyl groups, or
A and B form together a methylene group,
X is CH$_2$ or O,
n is 2 or 3
R$_4$ is a protected hydroxy group, and $R_5$ is a $(C_1-C_6)$alkyl group.

9. A method of preparing a compound of the general formula II, as defined in claim 8, wherein A and B form together a methylene group, characterized in that an ester compound of the general formula

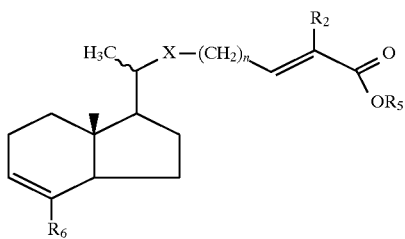 (IX)

wherein:
$R_2$, X and n have the meanings given in claim 1,
$R_5$ has the meaning given in claim 3, and
$R_6$ is a derivatized hydroxy group;
is reacted with an enyne compound of the general formula

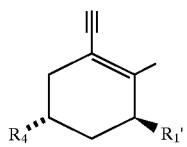 (VIII)

wherein $R_1'$ and $R_4$ have the meanings given in claim 3; followed by hydrogenation and isomerization.

10. A method of preparing a compound of the general formula II, as defined in claim 8, characterized in that a ketone of the general formula

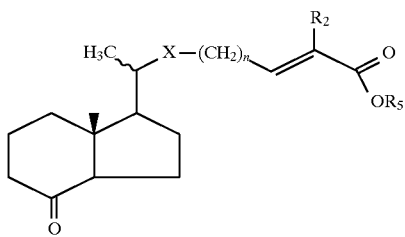 (X)

wherein:
$R_2$, X and n have the meanings given in claim 5, and
$R_5$ has the meaning given in claim 3;
is reacted with a Wittig reagent of the general formula

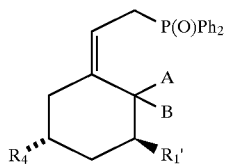 (VII)

wherein:
$R_1'$ and $R_4$ have the meanings given in claim 3, and
A and B have the meanings given in claim 1.

11. A method of preparing a compound of the general formula II as defined in claim 8, characterized in that a compound of the general formula

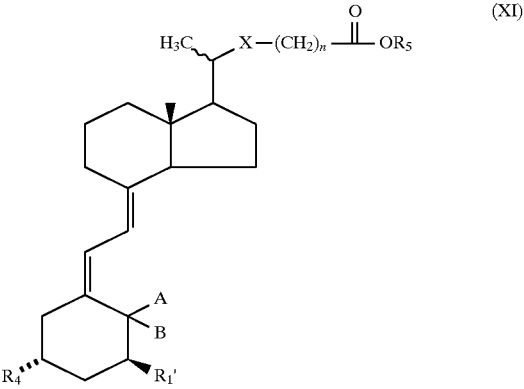 (XI)

is reacted with a reducing agent, after which the compound obtained, having the general formula

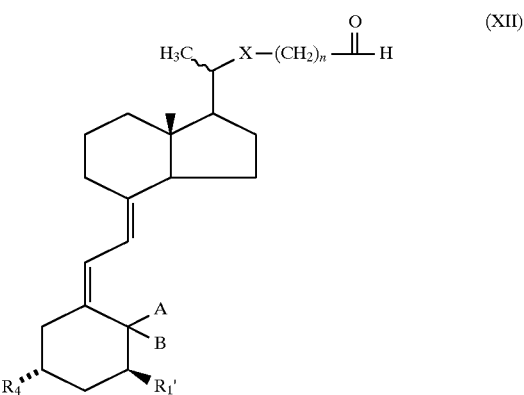 (XII)

is converted with a compound of the general formula

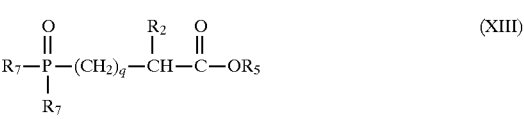 (XIII)

wherein:
$R_2$ has the meaning given in claim 1,
$R_5$ has the meaning given in claim 3,
$R_7$ is a substituent selected from the group consisting of branched or unbranched $(C_1-C_4)$alkoxy, phenoxy, phenyl or di$(C_1-C_4)$alkylamino, and
q is 0 or 1 if n is 1 and q is 0 if n is 2.

12. A method of preparing a compound of the general formula II as defined in claim 8, wherein:
$R_2$ is hydrogen,
A, B, X and n have the meanings as given in claim 1, and
$R_4$ and $R_5$ have the meanings given in claim 3;

characterized in that a compound of the general formula

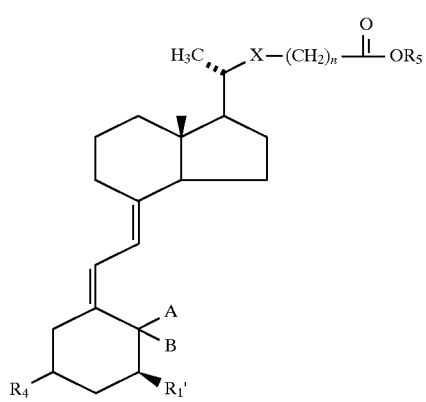

(XI)

is reacted with a reducing agent, after which the compound obtained, having the general formula

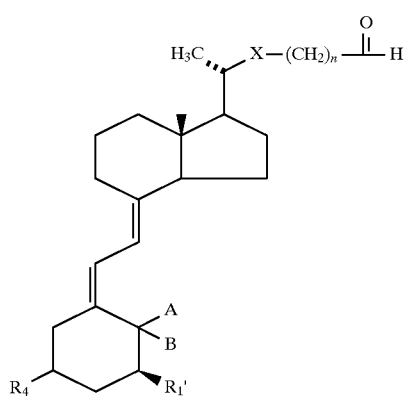

(XII)

is converted with a compound of the general formula

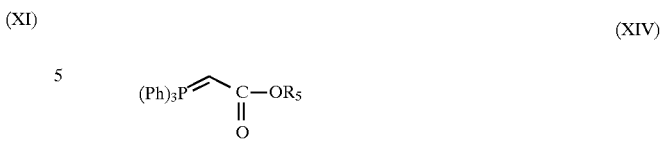

(XIV)

wherein:

$R_5$ has the meaning given in claim 3.

13. A method for the treatment of a number of disorders or diseases in a warm-blooded living being, comprising administering to said being or treating said being with a composition as claimed in claim 7 in a quantity effective for the intended purpose, wherein said disorders or diseases comprise: osteoporosis, renal osteodystrophy and osteomalacia; autoimmune diseases; acne skin aging; imbalance in the immune system; inflammatory diseases; diseases related to abnormal cell differentiation and/or proliferation; and solid, skin and blood cancers.

14. The method according to claim 13 wherein the inflammatory diseases are selected form the group consisting of rheumatoid arthritis and asthma.

15. A method for the treatment of alopecia comprising administering to a warm-blooded living being or treating said being with a composition as claimed in claim 7 in a quantity effective for the intended purpose.

* * * * *